United States Patent
Wellmann et al.

(10) Patent No.: US 6,849,578 B1
(45) Date of Patent: Feb. 1, 2005

(54) SELECTIVE HERBICIDES BASED ON 2,6-DISUBSTITUTED PYRIDINE DERIVATIVES

(75) Inventors: Arndt Wellmann, Odenthal (DE); Dieter Feucht, Monheim (DE); Mathias Kremer, Burscheid (DE); Birgit Krauskopf, Leawood, KS (US); Peter Dahmen, Neuss (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/130,387

(22) PCT Filed: Nov. 6, 2000

(86) PCT No.: PCT/EP00/10917

§ 371 (c)(1),
(2), (4) Date: May 14, 2002

(87) PCT Pub. No.: WO01/35740

PCT Pub. Date: May 25, 2001

(30) Foreign Application Priority Data

Nov. 17, 1999 (DE) ............................................. 199 55 128
Dec. 16, 1999 (DE) ............................................. 199 60 778

(51) Int. Cl.$^7$ ..................... A01N 43/40; A01N 43/653
(52) U.S. Cl. ............................ 504/130; 504/139; 504/254; 504/273; 504/274
(58) Field of Search ........................ 504/130, 139, 504/254, 273, 274, 263, 257

(56) References Cited

U.S. PATENT DOCUMENTS

| | | | |
|---|---|---|---|
| 3,671,523 A | 6/1972 | Westphal et al. | 260/248 AS |
| 3,910,909 A | 10/1975 | Draber et al. | 260/248 AS |
| 3,961,936 A | 6/1976 | Westphal et al. | 71/93 |
| 3,966,715 A | 6/1976 | Westphal et al. | 260/240 A |
| 4,036,632 A | 7/1977 | Westphal et al. | 71/93 |
| 4,509,971 A | 4/1985 | Forster et al. | 71/90 |
| 4,639,266 A | 1/1987 | Heubach et al. | 71/92 |
| 4,833,243 A | 5/1989 | Forster et al. | 540/480 |
| H670 H | 9/1989 | Kimura et al. | 71/92 |
| 4,881,966 A | 11/1989 | Nyffeler et al. | 71/94 |
| 4,968,342 A | 11/1990 | Forster et al. | 71/90 |
| 5,090,991 A | 2/1992 | Forster et al. | 71/90 |
| 5,190,576 A | 3/1993 | Bernard | 504/136 |
| 5,294,597 A * | 3/1994 | Foster et al. | 504/255 |
| 5,534,486 A | 7/1996 | Muller et al. | 504/273 |
| 5,541,337 A | 7/1996 | Muller et al. | 548/263.6 |
| 5,597,939 A | 1/1997 | Muller et al. | 558/8 |
| 5,648,315 A | 7/1997 | Lorenz et al. | 504/214 |
| 5,652,372 A | 7/1997 | Muller et al. | 548/263.4 |
| 5,674,807 A * | 10/1997 | Baltruschat | 504/130 |
| 5,700,758 A | 12/1997 | Rosch et al. | 504/106 |
| 5,824,624 A | 10/1998 | Kleeman et al. | 504/242 |
| 5,840,654 A | 11/1998 | Kleemann | 504/251 |
| 5,849,758 A | 12/1998 | Kleemann et al. | 514/269 |
| 5,858,920 A * | 1/1999 | Dahmen et al. | 504/103 |
| 5,869,681 A | 2/1999 | Muller et al. | 548/263.6 |
| 5,925,597 A | 7/1999 | Lorenz et al. | 504/212 |
| 6,008,161 A | 12/1999 | Kleemann et al. | 504/256 |
| 6,017,851 A | 1/2000 | Gut et al. | 504/133 |
| 6,066,597 A | 5/2000 | Kleemann et al. | 504/251 |
| 6,077,813 A | 6/2000 | Linker et al. | 504/272 |
| 6,239,306 B1 | 5/2001 | Lorenz et al. | 558/257 |
| 6,331,507 B1 | 12/2001 | Linker et al. | 504/244 |
| 2002/0028747 A1 * | 3/2002 | Baltruschat et al. | 504/138 |

FOREIGN PATENT DOCUMENTS

| | | |
|---|---|---|
| CA | 1013960 | 7/1977 |
| CA | 1 257 608 | 7/1989 |
| CA | 2 077 496 | 5/2003 |
| DE | 195 46 751 | 6/1996 |
| DE | 197 40 898 | 3/1998 |
| EP | 0 937 397 | 8/1999 |
| GB | 1085430 | 10/1967 |
| WO | 92/06962 | 4/1992 |
| WO | 94/22833 | 10/1994 |
| WO | 98/04134 | 2/1998 |
| WO | 98/04548 | 2/1998 |
| WO | 98/08383 | 3/1998 |

OTHER PUBLICATIONS

Weeds, 15 (month unavailable) 1967 pp. 20–22 Calculating Synergistic and Antagonistic Responses of Herbicide Combinations, S. R. Colby.

* cited by examiner

*Primary Examiner*—S. Mark Clardy
(74) *Attorney, Agent, or Firm*—Richard E. L. Henderson

(57) ABSTRACT

The present invention provides herbicidal synergistic active compound combinations comprising a 2,6-disubstituted pyridine of the formula (I)

and at least one herbicidally active compound and/or safeners. The synergistic active compound combinations of the present invention find use in the selective control of weed in various crops of plants.

5 Claims, No Drawings

SELECTIVE HERBICIDES BASED ON 2,6-DISUBSTITUTED PYRIDINE DERIVATIVES

FIELD OF THE INVENTION

The invention relates to novel herbicidal synergistic active compound combinations comprising, on the one hand, known 2,6-disubstituted pyridine derivatives and, on the other hand, known herbicidally active compounds and/or safeners and which can be used particularly successfully for the selective control of weeds in various crops of useful plants.

BACKGROUND OF THE INVENTION

As herbicides with broad action, 2,6-disubstituted pyridine derivatives form part of the subject-matter of a number of patent applications (cf. EP-A 447 004, WO-A 94/22833). However, the known pyridine derivatives have a number of gaps in their activity. The compatibility of these compounds with crop plants is likewise not entirely satisfactory under all conditions.

DETAILED DESCRIPTION OF THE INVENTION

Surprisingly, it has now been found that a number of known active compounds from the group of the 2,6-disubstituted pyridine derivatives, used jointly with known herbicidally active compounds from different substance classes, show pronounced synergistic effects with respect to the activity against weeds, and that such broadly active compound preparations can be used particularly advantageously for the selective control of weeds in crops of useful plants, such as, for example, wheat.

Surprisingly, it has also been found that the 2,6-disubstituted pyridine derivatives, on their own or together with known herbicidally active compounds, when used jointly with the crop-plant-compatibility-improving compounds (safeners/antidotes) described below, prevent damage to the crop plants particularly well and can be used particularly advantageously as a broadly active combination preparation for the selective control of weeds in crops of useful plants, for example cereal.

The invention provides selective herbicidal compositions, characterized in that they comprise an effective amount of an active compound combination comprising
(a) at least one 2,6-disubstituted pyridine derivative of the general formula (1)

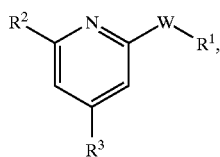

(I)

in which
$R^1$ represents a 5- or 6-membered heterocycle comprising 1 to 3 nitrogen atoms which is optionally mono- or polysubstituted by halogen and/or $C_1$–$C_3$-halogenoalkyl or represents a phenyl radical which is optionally mono- or polysubstituted by halogen and/or $C_1$–$C_3$-halogenoalkyl,
$R^2$ represents a phenoxy radical which is optionally substituted by halogen and/or $C_1$–$C_3$-halogenoalkyl,
$R^3$ represents a hydrogen atom or methyl, and
W represents oxygen or the group —CO—NH—,
("active compounds of group 1") and
(b) one or more compounds of a second group of herbicides comprising the active compounds mentioned below:
N-isopropyl-N-(4-fluorophenyl)-(5-trifluoromethyl-1,3,4-thiadiazol-2-yl-oxy)-acetamide (flufenacet, DE-38 21 600), 2-(2-methoxycarbonyl-phenylsulphonylaminocarbonyl)-4-methyl-5-n-propoxy-2,4-dihydro-3H-1,2,4-triazol-3-one or the sodium salt of this compound (propoxycarbazone-sodium, EP-A-507 171), 2-(2-trifluoromethoxy-phenylsulphonylaminocarbonyl)-4-methyl-5-methoxy-2,4-dihydro-3H-1,2,4-triazol-3-one or the sodium salt of this compound (flucarbazone-sodium, EP-A-507 171), N-(3,4-dichlorophenyl)propanamide (propanil, DE-A 1039779), N-2-benzothiazolyl-N,N'-dimethylurea (methabenzthiazuron, GB-A 1085430), 4-amino-6-(1,1-dimethylethyl)-3-(methylthio)-1,2,4-triazin-5(4H)-one (metribuzin, DE-A 1795784), 4-(2-chlorophenyl)-N-cyclohexyl-N-ethyl-4,5-dihydro-5-oxo-1H-tetrazol-1-carboxamide (fentrazamide, EP-A 612 735), 4-amino-3-methyl-6 phenyl-1,2,4-triazin-5 (4H)-one (metamitron, DE-A 2138031), 2-(2-benzo-thiazolyloxy)-N-methyl-N-phenylacetamide (mefenacet, DE-A2822155), 4-amino-6-(1,1-dimethylethyl)-3-(ethylthio)-1,2,4-triazin-5(4H)-one (ethiozin, DE-A 1542873) or 1-methylethyl 5-[4-bromo-1-methyl-5-(trifluoromethyl)-1H-pyrazol-3-yl]-2-chloro-4-fluorobenzoate (fluazolate, WO-A 9206962)
("active compounds of group 2"),
and optionally
(c) additionally at least one crop-plant-compatibility-improving compound from the following group of compounds:
α-(1,3-dioxolan-2-yl-methoximino)-phenylacetonitrile (oxabetrinil), α-(cyanomethoximino)-phenylacetonitrile (cyometrinil), 4-chloro-N-(1,3-dioxolan-2-yl-methoxy)-α-trifluoro-acetophenoneoxime (fluxofenim), 4,6-dichloro-2-phenyl-pyrimidine (fenclorim), 4-dichloroacetyl-3,4-dihydro-3-methyl-2H-1,4-benzoxazine (benoxacor), 1-methyl-hexyl 5-chloro-quinoxalin-8-oxy-acetate (cloquintocet), 2,2-dichloro-N-(2-oxo-2-(2-propenyl-amino)ethyl)-N-(2-propenyl)-acetamide (DKA-24), 1,8-naphthalic anhydride, ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 3-dichloroacetyl-5-(2-furanyl)-2,2-dimethyl-oxazolidine (furilazole, MON-13900), 4-dichloroacetyl-1-oxa-4-aza-spiro[4.5]-decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylaminocarbonylamino)-benzenesulphonamide, ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) (4-chloro-2-methyl-phenoxy)-acetic acid (MCPA), (+–)-2-(4- chloro-2-methylphenoxy)propanoic acid (mecoprop), 3-dichloroacetyl-2,2,5-trimethyl-oxazolidine (R-29148) and 2,4-dichlorophenoxyacetic acid (2,4-D) and its derivatives ("active compounds of group 3"), and optionally (d) additionally one or more compounds from a third group of herbicides comprising the active compounds mentioned below:

2-chloro-N-(ethoxymethyl)-N-(2-ethyl-6-methyl-phenyl) acetamide (acetochlor), 5-(2-chloro-4-trifluoromethyl-phenoxy)-2-nitro-benzoic acid sodium salt (acifluorfen-sodium), 2-chloro-6-nitro-3-phenoxy-benzenamine (aclonifen), 2-chloro-N-(methoxymethyl)-N-(2,6-diethyl-phenyl)-acetamide (alachlor), N-ethyl-N'-i-propyl-6-methylthio-1,3,5-triazine-2,4-diamine (ametryn), 4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methylsulphonyl-sulphamoyl)-urea (amidosulfuron), 1H-1,2,4-triazol-3-amine (amitrole), 6-chloro-4-ethylamino-2-isopropyl-amino-1,3,5-triazine (atrazine), 2-[2,4-dichloro-5-(2-propinyloxy)-phenyl]-5,6,7,8-tetrahydro-1,2,4-triazolo-[4,3-a]-pyridin-3 (2H)-one (azafenidin), N-(4,6-dimethoxy-pyrimidin-2-yl)-N'-[1-methyl-4-(2-methyl-2H-tetrazol-5-yl)-1H-pyrazol-5-ylsulphonyl]-urea (azimsulfuron), N-benzyl-2-(4-fluoro-3-trifluoromethyl-phenoxy)-butanamide (beflubutamide), 4-chloro-2-oxo-3(2H)-benzothiazoleacetic acid (benazolin), N-butyl-N-ethyl-2,6-dinitro-4-tri-fluoromethyl-benzenamine (benfluralin), N-(4,6-dimethoxy-pyrimidin-2-yl)-N'-(2-methoxycarbonyl-phenylmethylsulphonyl)-urea (bensulfuron), methyl 2-[2-[4-(3,6-dihydro-3-methyl-2,6-dioxo-4-tri fluoromethyl-1(2H)-pyrimidin-yl) phenoxy]methyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), ethyl N-benzoyl-N-(3,4-dichloro-phenyl)-DL-alaninate (benzoylprop-ethyl), 3-i-propyl-1H-2,1,3-benzothiadiazin-4(3H)-one (bentazone), methyl 5-(2,4-dichloro-phenoxy)-2-nitrobenzoate (bifenox), 2,6-bis-(4,6-dimethoxy-pyrimidin-2-yl-oxy)-benzoic acid sodium salt (bispyribac-sodium), 2-bromo-3,3-dimethyl-N-(1-methyl-1-phenyl-ethyl) butanamide (bromobutide), O-(2,4-dinitro-phenyl) 3,5-dibromo-4-hydroxy-benzaldehyde-oxime (bromofenoxim), 3,5-dibromo-4-hydroxy-benzonitrile (bromoxynil), N-butoxymethyl-2-chloro-N-(2,6-diethyl-phenyl)-acetamide (butachlor), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), S-ethyl bis-(2-methyl-propyl) thiocarbamate (butylate), N,N-diethyl-3-(2,4,6-trimethyl-phenylsulphonyl) 1H-1,2,4-triazole-1-carboxamide (cafenstrole), 2-[1-[(3-chloro-2-propenyl oxy-imino]-propyl]-3-hydroxy-5-(tetrahydro-2H-pyran-4-yl)-2-cyclohexen-1-one (caloxydim, tepraloxydim), 2,4-chloro-2-fluoro-5-(2-chloro-2-ethoxy-carbonyl-ethyl)-phenyl]-4-difluoromethyl-5-methyl-2,4-dihydro-3H-1, 2,4-triazol-3-one (carfentrzone-ethyl), 2,4-dichloro-1-(3-methoxy-4-nitro-phenoxy) benzene (chlomethoxyfen), 3-amino-2,5-dichloro-benzoic acid (chloramben), N-(4-chloro-6-methoxy-pyrimidin-2-yl)-N'-(2-ethoxycarbonyl-phenylsulphonyl)-urea (chlorimuron-ethyl), 1,3,5-trichloro-2-(4-nitro-phenoxy)-benzene (chlornitrofen), N-(4-methoxy-6-methyl-1,3,5-triazin-2-yl)-N'-(2-chloro-phenylsulphonyl)-urea (chlorsulfuron), N'-(3-chloro-4-methyl-phenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), N-(4,6-dimethoxy-1,3,5-triazin-2-yl)-N'-(2-(2-methoxy-ethoxy)-phenylsulphonyl)-urea (cinosulfuron), 2-[1-[2-(4-chloro-phenoxy)-propoxyamino]butyl]-5-(tetrahydro-2H-thiopyran-3-yl)-1,3-cyclo-hexanedione (clefoxydim), (E,E)-(+)-2-[1-[[(3-chloro-2-propenyl)-oxy]-imino]-propyl]-3-hydroxy-2-cyclohexen-1-one (clethodim), prop-2-inyl (R)-2-[4-(5-chloro-3-fluoro-pyridin-2-yl-oxy)-phenoxy]-propanoate (clodinafop-propargyl), 3,6-dichloro-pyridine-2-carboxylic acid (clopyralid), methyl 3-chloro-2-[(5-ethoxy-7-fluoro[1,2,4]triazolo [1,5-c]pyrimidin-2-yl-sulphonyl)-amino]-benzoate (cloransulam-methyl), 2-chloro-4-ethylamino-6-(1-cyano-1-methyl-ethylamino)-11,3,5-triazine (cyanazine), N-(4,6-dimethoxy-pyrimidin-2-yl)-N'-(2-cyclopropylcarbonyl-phenylsulphonyl)-urea (cyclosulfamuron), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), 2,4-dichloro-phenoxy-acetic acid (2,4-D), 3,6-dichloro-2-methoxy-benzoic acid (dicamba), (R)-2-(2,4-dichloro-phenoxy)-propanoic acid (dichlorprop-P), methyl-2-[4-(2,4-dichloro-phenoxy)phenoxy]-propanoate (diclofop-methyl), N-(2,6-dichloro-phenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methyl-sulphate (difenzoquat), N-(2,4-difluoro-phenyl)-2-(3-trifluoromethyl-phenoxy)-pyridine-3-carboxamide (diflufenican), 2-[1-[(3,5-difluoro-phenyl) amino-carbonyl-hydrazono]-ethyl]-pyridine-3-carboxylic acid (diflufenzopyr), S-(1-methyl-1-phenyl-ethyl) 1-piperidine-carbothioate (dimepiperate), (S-) 2-chloro-N-(2,4-dimethyl-3-thienyl)-N-(2-methoxy-1-methyl-ethyl)-acetamide(S-) (dimethenamid), 2-amino-4-(1-fluoro-1-methyl-ethyl)-6-(1-methyl-2-(3,5-dimethyl-phenoxy)-ethylamino)-1,3,5-triazine (dimexyflam), N3,N3-diethyl-2,4-dinitro-6-trifluoromethyl-1,3-diamino-benzene (dinitramine), 6,7-dihydro-dipyrido[1,2-a:2',1'-c]pyrazinediium (diquat), S,S-dimethyl 2-difluoromethyl-4-i-butyl-6-trifluoromethyl-pyridine-3,5-dicarbothioate (dithiopyr), N'-(3,4-dichloro-phenyl)-N,N-dimethyl-urea (diuron), 2-[2-(3-chloro-phenyl)-oxiranylmethyl]-2-ethyl-1H-indene-1,3(2H)-dione (epropodan), S-ethyl dipropylthiocarbamate (EPTC), S-(phenylmethyl) N-ethyl-N-(1,2-dimethyl-propyl)-thiocarbamate (esprocarb), N-ethyl-N-(2-methyl-2-propenyl)-2,6-dinitro-4-trifluoromethyl-benzenamine (ethalfluralin), 2-ethoxy-1-methyl-2-oxoethyl (S)-2-chloro-5-(2-chloro-4-trifluoromethyl-phenoxy)benzoate (ethoxyfen), N-(4,6-dimethoxy-pyrimidin-2-yl)-N'-(2-ethoxy-phenoxysulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamide), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluoro-benzoate (fluazolate), 4,5-dihydro-3-methoxy-4-methyl-5-oxo-N-[(2-trifluoromethoxy-phenyl)-sulphonyl]-1-H-1,2,4-triazole-1-carboxamide sodium salt (flucarbazone-sodium), N-(4-fluoro-phenyl)-N-i-propyl-2-(5-trifluoromethyl-1,3,4-thiadiazol-2-yl-oxy)-acetamide (flufenacet), N-(2,6-difluoro-phenyl)-5-methyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H-isoindol-2-yl)phenoxy]-acetate (flumiclorac-pentyl), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propinyl)-oxy]-phenyl]-4,5,6,7-tetrahydro-1H-isoindole-1,3(2H)-dione (flumipropyn), 3-chloro-4-chloromethyl-1-(3-trifluoromethyl-phenyl)-2-pyrrolidinone (fluoro-chloridone), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-penta-fluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-tri-fluoromethyl-1(2H)-pyrimidyl) benzoate (flupropacil), N-(4,6-diethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-fluorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxypropyl, -meptyl), 5-methylamino-2-phenyl-4-(3-trifluoromethyl-phenyl)-3(2H)-furanone (flurtamone), methyl[[(2-chloro-4-fluoro-5-(tetrahydro-3-oxo-1H,3H-[1,3,4]-thiadiazolo-[3,4-a]-pyridazin-1-ylidene)amino]-phenyl]-thio-acetate (fluthiacet-methyl), 5-(2-chloro-4-trifluoromethyl-phenoxy)-N-methylsulphonyl-2-nitro-benzamide (fomesafen), 2-[[[[(4,6-dimethoxy-2-pyrimidinyl)-amino]-carbonyl]-amino]-sulphonyl]-4-formyl-amino-N,N-dimethyl-benzamide (foramsulfuron), 2-amino-4-(hydroxymethyl-phosphinyl)-butanoic acid (ammonium salt) (glufosinate-(ammonium)), N-phosphonomethyl-glycine (isopropylammonium salt), (glyphosate, isopropylammonium), (R)-2-[4-(3-chloro-5-trifluoromethyl-pyridin-2-yl-oxy)-phenoxy]-propanoic acid (methyl ester, 2-ethoxy-ethyl ester, butyl ester) (haloxyfop, -methyl, -P-methyl, -ethoxyethyl, -butyl), 3-cyclohexyl-6-di-methylamino-1-methyl-1,3,5-triazine-2,4(1H,3H1)-dione (hexazinone), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), N-(4-methoxy-6-methyl-1,3,5-triazin-2-yl)-N'-(5-iodo-2-methoxy-carbonyl-phenylsulphonyl)-urea sodium salt (iodosulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (4-chloro-2-methylsulphonyl-phenyl)-(5-cyclopropyl-isoxazol-4-yl)-methanone (isoxachlortole), (5-cyclopropyl-isoxazol-4-yl)-2-methylsulphonyl-4-trifluoromethyl-phenyl)-methanone (isoxaflutole), 2-[2-[4-[(3,5-dichloro-2-pyridinyl)-oxy]-phenoxy]-1-oxo-propyl]-isoxazolidine (isoxapyrifop), (2-ethoxy-1-methyl-2-oxo-ethyl)-5-(2-chloro-4-trifluoromethyl-phenoxy)-2-nitro-benzoate (lactofen), N'-(3,4-dichlorophenyl)-N-methoxy-N-methyl-urea (linuron), (4-chloro-2-methyl-phenoxy)-acetic acid (MCPA), 2-(4-chloro-2-methyl-phenoxy)-propionic acid (mecoprop), 2-(2-benzothiazolyloxy)-N-methyl-N-phenyl-acetamide (mefenacet), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)phenyl)-N-methoxy-N-methyl-urea (metobenzuron), N'-(4-bromo-phenyl)-N-methoxy-N-methyl urea (metobromuron), (S-)-2-chloro-N-(2-ethyl-6-methyl-phenyl)-N-(2-methoxy-1-methyl-ethyl)-acetamide (metolachlor, S-metolachlor), N-(2,6-dichloro-3-methyl-phenyl)-5,7-dimethoxy-1,2,4-triazolo[1,5-a]-pyrimidine-2-sulphonamide (metosulam), N'-(3-chloro-4-methoxy-phenyl)-N,N-dimethyl-urea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), S-ethyl-hexahydro-1H-azepine-1-carbothioate (molinate), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), S-(2-chloro-benzyl)-N,N-diethyl-thiocarbamate (orbencarb), 4-dipropylamino-3,5-dinitro-benzenesulphonamide (oryzalin), 3-[2,4-dichloro-5-(2-propinyl-oxy)-phenyl]-5-(t-butyl)-1,3,4-oxadiazol-2(3H)-one (oxadiargyl), 3-[2,4-dichloro-5-(1-methyl-ethoxy)phenyl]-5-(t-butyl)-1,3,4-oxadiazol-2(3H)-one (oxadiazon), N-(4,6-dimethyl-pyrimidin-2-yl)-N'-(2-oxetan-3-yl-oxycarbonyl-phenylsulphonyl)-urea (oxasulfuron), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethylbenzene (oxyfluorfen), 1,1'-dimethyl-4,4'-bipyridinium (paraquat), 1-amino-N-(1-ethyl-propyl)-3,4-dimethyl-2,6-dinitro-benzene (pendimethalin), 4-(t-butyl)-N-(1-ethyl-propyl)-2,6-dinitro-benzenamine (pendralin), 4-amino-3,5,6-trichloro-pyridine-2-carboxylic acid (picloram), 2-chloro-N-(2,6-diethyl-phenyl)-N-(2-propoxy-ethyl)-acetamide (pretilachlor), N-(4,6-bisdifluoromethoxy-pyrimidin-2-yl)-N'-(2-methoxycarbonyl-phenylsulphonyl)-urea (primisulfuron-methyl), 1-chloro-N-[2-chloro-4-fluoro-5-[(6S,7aR)-6-fluoro-tetrahydro-1,3-dioxo-1H-pyrrolo[1,2-c]imidazol-2(3H)-yl]-phenyl]-methanesulphonamide (profluazol), 2-chloro-N-isopropyl-N-phenyl-acetamide (propachlor), N-(3,4-dichloro-phenyl)-propanamide (propanil), (R)-[2-[[(1-methyl-ethylidene)-amino]-oxy]-ethyl]-2-[4-(6-chloro-2-quinoxalinyloxy)-phenoxy]-propanoate (propaquizafop), 2-chloro-N-(2-ethyl-6-methyl-phenyl)-N-[(1-methyl-ethoxy)methyl]-acetamide (propisochlor), methyl 2-[[[(4,5-dihydro-4-methyl-5-oxo-3-propoxy-1H-1,2,4-triazol-1-yl) carbonyl]-amino]-sulphonyl]-benzoate sodium salt (propoxycarbazone-sodium), S-phenyl-methyl N,N-dipropyl-thiocarbamate (prosulfocarb), N-(4-methoxy-6-methyl-1,3,5-triazin-2-yl)-N'-(2-(3,3,3-trifluoro-propyl)-phenylsulphonyl)-urea (prosulfuron), ethyl [2-chloro-5-(4-chloro-5-difluoromethoxy-1-methyl-1H-pyrazol-3-yl)-4-fluoro-phenoxy]-acetate (pyraflufen-ethyl), 1-(3-chloro-4,5,6,7-tetrahydro-pyrazolo[1,5-a]pyridin-2-yl)-5-methyl-2-propinylamino)-1H-pyrazole-4-carbonitrile (pyrazogyl), 4-(2,4-dichloro-benzoyl)-1,3-dimethyl-5-(4-methyl-phenylsulphonyloxy)-pyrazole (pyrazolate), 4-(2,4-dichloro-benzoyl)-1,3-dimethyl-5-(phenylcarbonylmethoxy)-pyrazole (pyrazoxyfen), N-(4,6-di-methoxy-pyrimidin-2-yl)-N'-(4-ethoxycarbonyl-1-methyl-pyrazol-5-yl-sulphonyl)-urea (pyrazosulfuron-ethyl), O-[2,6-bis-(4,6-dimethoxy-pyrimidin-2-yl-oxy)benzoyl] diphenylmethanone-oxime (pyribenzoxim), 6-chloro-3-phenyl-4-pyridazinol (pyridafol), O-(6-chloro-3-phenyl-pyridazin-4-yl)S-octyl thiocarbonate (pyridate), 6-chloro-3-phenylpyridazin-4-ol (pyridatol), 7-[(4,6-dimethoxy-2-pyrimidinyl)-thio]-3-methyl-[(3H)-isobenzofuranone (pyriftalid), methyl 2-(4,6-dimethoxy-pyrimidin-2-yl-oxy)-benzoate (pyriminobac-methyl), 2-chloro-6-(4,6-dimethoxy-pyrimidin-2-yl-thio)-benzoic acid sodium salt (pyrithiobac-sodium), 3,7-dichloro-quinoline-8-carboxylic acid (quinchlorac), 7-chloro-3-methyl-quinoline-8-carboxylic acid (quinmerac), 2-[4-(6-chloro-2-quinoxalinyloxy)-phenoxy]-propanoic acid (ethyl ester, tetrahydro-2-furanyl-methyl ester) (quizalofop, -ethyl, -P-ethyl, -P-tefuryl), N-(4,6-dimethoxy-pyrimidin-2-yl)-N'-(3-ethylsulphonyl-pyridin-2-yl-sulphonyl)-urea (rimsulfuron), 2(1-ethoximinobutyl)-5-(2-ethyl-thiopropyl)-3-hydroxy-2-cyclohexen-1-one (sethoxydim), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonyl-amino-phenyl)-4-difluoromethyl-5-methyl-2,4-dihydro-3H-1,2,4-triazol-3-one (sulfentrazone), N-phosphonomethyl-glycine-trimethylsulphonium (sulfosate), N-(4,6-dimethoxy-pyrimidin-2-yl)-N'-(2-ethylsulphonyl)-imidazo[1,2-a]-pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)acetamide (thenylchlor), methyl 2-difluoro-methyl-5-(4,5-dihydro-thiazol-2-yl)-4-(2-methyl-propyl)-6-trifluoromethyl-pyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propinyl)-2H-1,4-benzoxazin-3(4H)-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropyl-carbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), (3,5,6-trichloro)-pyridin-2-yl-oxy-acetic acid (triclopyr), 2-(3,5-dichloro-phenyl)-2-(2,2,2-trichloro-ethyl)-oxirane (tridiphane), N-[[(4,6-dimethoxy-2-pyrimidinyl)-amino]-carbonyl]-3-(2,2,2-trifluoro-ethoxy)-2-pyridinesulphonamide sodium salt (trifloxysulfuron), 1-amino-2,6-dinitro-N,N-dipropyl-4-trifluoromethyl-benzene (trifluralin), N-[4-dimethylamino-6-(2,2,2-trifluoro-ethoxy)-1,3,5-triazin-2-yl]-N'-(2-methoxy-carbonyl-phenylsulphonyl)-urea (triflusulfuron-methyl), N-(4-methoxy-6-trifluoromethoxy-1,3,5-triazin-2-yl)-N'-(2-trifluoromethyl-phenylsulphonyl)-urea (tritosulfuron), 2-pyridinesulphonamide N-[[(4,6-dimethoxy-2-pyrimidinyl)amino]carbonyl]-3-(N-methyl-N-methylsulphonyl-amino) (cf. WO-A-92/10660), 2-[[[[(4,6-dimethoxy-2-pyrimidinyl)amino]carbonyl] amino]-sulphonyl]-4-[[(methylsulphonyl)amino] methyl]-methyl benzoate (cf. DE-A 43 35 297), 4-[4,5-dihydro-4-methyl-5-oxo-(3-trifluoromethyl)-1H-1,2,4-triazol-1-yl]-2-[(ethylsulphonyl)amino]-5-fluoro-benzenecarbothioamide (cf. WO-A-95/30661)

("active compounds of group 4"), where the compound under (b) does not represent flufenacet if the compound under (a) is 2-(3,4-difluorophenoxy)-4-methyl-6-(1-methyl-3-trifluoromethyl-pyrazol-5-yl)-pyridine.

Preferred substituents of the radicals listed in formula (I) shown above are illustrated below.

$R^1$ preferably represents a pyrazolyl radical which is optionally mono- or polysubstituted by trifluoromethyl and methyl or represents a phenyl radical which is optionally mono- or polysubstituted by fluorine.

$R^2$ preferably represents an optionally halogen- and/or $C_1$–$C_3$-halogenoalkyl-substituted phenoxy radical.

$R^3$ preferably represents a hydrogen atom or methyl.

W preferably represents oxygen or the group —CO—NH—.

Among the active compounds of group 3, particular emphasis is given to the following mixing components:

1-methylhexyl 5-chloro-quinoxalin-8-oxy-acetate (cloquintocet), ethyl 1-(2,4-dichloro-phenyl)-5-trichloromethyl-1H-1,2,4-triazole-3-carboxylate (fenchlorazol-ethyl), ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) and 2,4-dichlorophenoxyacetic acid (2,4-D) and its derivatives.

As described, the activity properties of the combinations described above can be improved even more, if appropriate, by adding a compound from the third group of herbicides ("active compounds of group 4"). Among the "active compounds of group 4", particular emphasis is given to the following mixing components:

4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methylsulphonyl-sulphamoyl)-urea (amidosulfuron), N-benzyl-2-(4-fluoro-3-trifluoromethyl-phenoxy)-butanamide (beflubutamide), 3-i-propyl-1H-2,1,3-benzothiadiazin-4(3H)-one (bentazone), methyl 5-(2,4-dichloro-phenoxy)-2-nitrobenzoate (bifenox), 2,6-bis-(4,6-dimethoxy-pyrimidin-2-yl-oxy)-benzoic acid sodium salt (bispyribac-sodium), 3,5-dibromo-4-hydroxy-benzonitrile (bromoxynil), N-butoxymethyl-2-chloro-N-(2,6-diethyl-phenyl)-acetamide (butachlor), [1,1-dimethyl-2-oxo-2-(2-propenyloxy)]-ethyl 2-chloro-5-(3,6-dihydro-3-methyl-2,6-dioxo-4-tri-fluoromethyl-1(2H)-pyrimidinyl)-benzoate (butafenacil-allyl), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), N-(4-methoxy-6-methyl-1,3,5-triazin-2-yl)-N'-(2-chloro-phenylsulphonyl)-urea (chlorsulfuron), N'-(3-chloro-4-methyl-phenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), prop-2-inyl (R)-2-[4-(5-chloro-3-fluoro-pyridin-2-yl-oxy)-phenoxy]-propanoate (clodinafop-propargyl), 3,6-dichloro-pyridine-2-carboxylic acid (clopyralid), 2-chloro-4-ethylamino-6-(1-cyano-1-methyl-ethylamino)-1,3,5-triazine (cyanazine), N-(4,6-dimethoxy-pyrimidin-2-yl)-N-(2-cyclopropylcarbonyl-phenylsulphonyl)-urea (cyclosulfamuron), 2,4-dichloro-phenoxyacetic acid (2,4-D), 3,6-dichloro-2-methoxy-benzoic acid (dicamba), (R)-2-(2,4-dichloro-phenoxy)propanoic acid (dichlorprop-P), methyl-2-[4-(2,4-dichloro-phenoxy)-phenoxy]-propanoate (diclofop-methyl), 1,2-dimethyl-3,5-diphenyl-1H-pyrazolium methylsulphate (difenzoquat), 2-ethoxy-1-methyl-2-oxoethyl (S)-2-chloro-5-(2-chloro-4-trifluoromethyl-phenoxy)-benzoate (ethoxyfen), N-(4,6-dimethoxy-pyrimidin-2-yl)-N'-(2-ethoxy-phenoxy-sulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamid), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo[1,5-c]-pyrimidine-2-sulphonamide (florasulam), i-propyl 5-(4-bromo-1-methyl-5-trifluoromethyl-1H-pyrazol-3-yl)-2-chloro-4-fluoro-benzoate (fluazolate), 4,5-dihydro-3-methoxy-4-methyl-5-oxo-N-[(2-trifluoromethoxy-phenyl)-sulphonyl]-1-H-1,2,4-triazole-1-carboxamide sodium salt (flucarbazone-sodium), N-(4-fluoro-phenyl)-N-1-propyl-2-(5-trifluoromethyl-1,3,4-thiadiazol-2-yl-oxy)-acetamide (flufenacet), N-(2,6-difluoro-phenyl)-5-methyl-1,2,4-triazolo[1,5-a]-pyrimidine-2-sulphonamide (flumetsulam), ethoxycarbonyl-methyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)phenyl)-5-phenyl-1H-1,2,4-triazole-3-carboxamide (flupoxam), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-fluorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxypropyl, -meptyl), 5-methylamino-2-phenyl-4-(3-trifluoromethyl-phenyl)-3(2H)-furanone (flurtamone), 2-amino-4-(hydroxymethylphosphinyl)-butanoic acid (ammonium salt) (glufosinate-(ammonium)), N-phosphonomethyl-glycine (isopropylammonium salt), (glyphosate, isopropylammonium), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-i-propyl-5-oxo-1H-imidazol-2-yl)-5-ethyl-pyridine-3-carboxylic acid (imazethapyr), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl) 2,6-dimethoxy-benzamide (isoxaben), (4-chloro-2-methyl-phenoxy)-acetic acid (MCPA), 2-(4-chloro-2-methyl-phenoxy)-propionic acid (mecoprop), 2-(2-benzo thiazolyloxy)-N-methyl-N-phenyl-acetamide (mefenacet), 4-amino-3-methyl-6-phenyl-1,2,4-triazin-5 (4H)-one (metamitron), N-(2,6-dichloro-3-methyl-phenyl)-5,7-dimethoxy-1,2,4-triazolo[1,5-a]-pyrimidine-2-sulphonamide (metosulam), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), 1-amino-N-(1-ethyl-propyl)-3,4-dimethyl-2,6-dinitro-benzene (pendimethalin), N-(3,4-dichloro-phenyl)-propanamide (propanil), methyl 2-[[[(4,5-dihydro-4-methyl-5-oxo-3-propoxy-1H-1,2,4-triazol-1-yl) carbonyl]amino]sulphonyl]-benzoate sodium salt (propoxycarbazone-sodium), S-phenylmethyl N,N-dipropyl-thiocarbamate (prosulfocarb), ethyl [2-chloro-5-(4-chloro-5-difluoromethoxy-1-methyl-1H-pyrazol-3-yl)-4-fluoro-phenoxy]-acetate (pyraflufen-ethyl), 7-chloro-3-methyl-quinoline-8-carboxylic acid (quinmerac), N-phosphonomethyl-glycine-trimethylsulphonium (sulfosate), N-(4,6-dimethoxy-pyrimidin-2-yl)-N-(2-ethyl-sulphonyl)-imidazo[1,2-a] pyridine-3-sulphonamide (sulfosulfuron), 2-tert-butyl-amino-4-ethylamino-6-methylthio-1,3,5-triazine (terbutryn), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)phenyl-sulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), N-[[(4,6-dimethoxy-2-pyrimidinyl)amino]carbonyl]-3-(2,2,2-trifluoro-ethoxy)-2-pyridin-sulphonamide sodium salt (trifloxysulfuron), 1-amino-2,6-dinitro-N,N-dipropyl-4-trifluoromethyl-benzene (trifluralin), N-(4-methoxy-6-trifluoromethoxy-1,3,5-triazin-2-yl)-N'-(2-tri fluoromethyl-phenylsulphonyl)-urea (tritosulfuron)

Very particular preference according to the invention is given to selective herbicidal compositions which are characterized in that they comprise an active compound combination comprising a) N-(4-fluorophenyl)-6-[3-(trifluoromethyl)phenoxy]-2-pyridinecarboxamide (picolinafen) or 2-(3,4- difluorophenoxy)-4-methyl-6-(1-methyl-3-trifluoro-methylpyrazol-5-yl)-pyridine and
b) one or more compounds from a second group of herbicides which contains the active compounds mentioned above under (b) ("active compounds of group 2"),
    where the compound from group (b) does not represent flufenacet if the compound (a) is 2-(3,4-difluorophenoxy)-4-methyl-6-(1-methyl-3-trifluoro-methylpyrazol-5-yl)-pyridine,
and optionally
c) at least one of the abovementioned crop-plant-compatibility-improving compounds of the active compounds of group 3, where preference is given to those compounds which were emphasized above.

Most preference according to the invention is given to the selective herbicidal compositions which comprise, as compound of the active compounds of group 1, picolinafen.

Emphasis is furthermore given to selective herbicidal compositions which are characterized in that they comprise an active compound combination comprising
(a) picolinafen and
(b) N-isopropyl-N-(4-fluorophenyl)-(5-trifluoromethyl-1,3,4-thiadiazol-2-yl-oxy)-acetamide (flufenacet) and
(c) optionally one or more compounds from the group consisting of 2,6-bis-(4,6-dimethoxy-pyrimidin-2-yl-oxy)-benzoic acid sodium salt (bispyribac-sodium), N-(2,6-difluoro-phenyl)-8-fluoro-5-methoxy-[1,2,4]-triazolo-[1,5-c]-pyrimidine-2-sulphonamide (florasulam), N-(4,6-dimethoxy-pyrimidin-2-yl)-N'-(3-methoxycarbonyl-6-trifluoromethyl-pyridin-2-yl-sulphonyl)-urea sodium salt (flupyrsulfron-methyl-sodium), N,N-dimethyl-N'-(4-isopropyl-phenyl)-urea (isoproturon), N-(2,6-dichloro-3-methyl-phenyl)-5,7-dimethoxy-1,2,4-triazolo[1,5-a]-pyrimidine-2-sulphonamide (metosulam), 1-amino-N-(1-ethyl-propyl)-3,4-dimethyl-2,6-dinitro-benzene (pendimethalin) and ethyl-[2-chloro-5-(4-chloro-5-difluoromethoxy-1-methyl-1H-pyrazol-3-yl)-4-fluoro-phenoxy]-acetate (pyraflufen-ethyl).

Emphasis is also given to selective herbicidal compositions which are characterized in that they comprise an active compound combination comprising
(a) picolinafen and
(b) 2-(2-methoxycarbonylphenylsulphonylaminocarbonyl)-4-methyl-5-n-propoxy-2,4-dihydro-3H-1,2,4-triazol-3-one or the sodium salt of this compound (propoxycarbazone-sodium) and
(c) optionally one or more compounds from the group consisting of N-(4,6-dimethoxy-pyrimidin-2-yl)-N'-(N-methyl-N-methylsulphonyl-sulphamoyl)-urea (amidosulfuron), 2,6-bis-(4,6-dimethoxy-pyrimidin-2-yl-oxy)-benzoic acid sodium salt (bispyribac-sodium), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), ethyl 2-chloro-3-[2-chloro-5-(1,3,4,5,6,7-hexahydro-1,3-dioxo-2H-isoindol-2-yl)-phenyl]-2-propanoate (cinidon-ethyl), 2-chloro-4-ethylamino-6-(1-cyano-1-methyl-ethylamino)-1,3,5-triazine (cyanazine), 2,4-dichloro-phenoxyacetic acid (2,4-D), (R)-2-(2,4-dichloro-phenoxy)-propanoic acid (dichlorprop-P), N-(2,6-difluoro-phenyl)-8-fluoro-5-methoxy-[1,2,4]-triazolo-[1,5-c]-pyrimidine-2-sulphonamide (florasulam), N-(4-fluoro-phenyl)-N-1-propyl-2-(5-trifluoromethyl-1,3,4-thiadiazol-2-yl-oxy) acetamide (flufenacet), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), (4-amino-3,5-dichloro-6-fluoro-pyridin-2-yl-oxy)-acetic acid (-2-butoxy-1-methyl-ethyl ester, -1-methyl-heptyl ester) (fluroxypyr, -butoxypropyl, -meptyl), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), N,N-dimethyl-N'-(4-iso-propyl-phenyl)-urea (isoproturon), 2-(4-chloro-2-methyl-phenoxy)propionic acid (mecoprop), N-(2,6-dichloro-3-methyl-phenyl)-5,7-dimethoxy-1,2,4-triazolo[1,5-a]-pyrimidine-2-sulphonamide (metosulam), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), 1-amino-N-(1-ethyl-propyl)-3,4-dimethyl-2,6-dinitro-benzene (pendimethalin), N-(4-methoxy-6-methyl-1,3,5-triazin-2-yl)-N'-(2-methoxy-carbonyl-thien-3-yl-sulphonyl)-urea (thifensulfuron-methyl), N-methyl-N-(4-methoxy-6-methyl-1,3,5-triazin-2-yl]N'-(2-methoxycarbonyl-phenylsulphonyl)-urea (tribenuron-methyl), N-[[(4,6-dimethoxy-2-pyrimidinyl)-amino]carbonyl]-3-(2,2,2-trifluoro-ethoxy)-2-pyridinesulfonamide sodium salt (trifloxysulfuron), N-(4-methoxy-6-trifluoromethoxy-1,3,5-triazin-2-yl)-N'-(2-trifluoromethyl-phenylsulphonyl)-urea (tritosulfuron).

Emphasis is also given to selective herbicidal compositions which are characterized in that they comprise an active compound combination comprising
(a) picolinafen and
(b) 2-(2-trifluoromethoxy-phenylsulphonylaminocarbonyl)-4-methyl-5-methoxy-2,4-dihydro-3H-1,2,4-triazol-3-one or the sodium salt of this compound (flucarbazone-sodium) and
(c) optionally one or more compounds from the group consisting of 2,6-bis-(4,6-dimethoxy-pyrimidin-2-yl-oxy)-benzoic acid sodium salt (bispyribac-sodium), 3,5-dibromo-4-hydroxy-benzonitrile (bromoxynil), 2-(4-chloro-2-fluoro-5-(2-chloro-2-ethoxycarbonyl-ethyl)-phenyl)-4-difluoromethyl-5-meth-yl-2,4-dihydro-3H-1,2,4-triazol-3-one (carfentrazone-ethyl), ethyl 2-chloro-3-[2-chloro-5-(1,3,4,5,6,7-hexahydro-1,3-dioxo-2H-isoindol-2-yl)-phenyl]-2-propanoate (cinidon-ethyl), 2-propinyl (R)-2-[4-(5-chloro-3-fluoro-pyridin-2-yl-oxy)-phenoxy-propanoate (clodinafop-propargyl), 3,6-dichloropyridine-2-carboxylic acid (clopyralid), 2,4-dichloro-phenoxyacetic acid (2,4-D), 3,6-dichloro-2-methoxy-benzoic acid (dicamba), ethyl (R)-2-[4-(6-chloro-benzoxazol-2-yl-oxy)-phenoxy]-propanoate (fenoxaprop-(P)-ethyl), N-(2,6-difluoro-phenyl)-8-fluoro-5-methoxy-[1,2,4]-triazolo-[1,5-c]-pyrimidine-2-sulphonamide (florasulam), N-(4-fluoro-phenyl)-N-1-propyl-2-(S-trifluoromethyl-1,3,4-thiadiazol-2-yl-oxy)-acetamide (flufenacet), N-(4,6-dimethoxy-pyrimidin-2-yl)-N'-(3-methoxycarbonyl-6-trifluoromethyl-pyridin-2-yl-sulphonyl) urea sodium salt (flupyrsulfuron-methyl-sodium), (4-amino-3,5-dichloro-6 fluoro-pyridin-2-yl-oxy)-acetic acid (-2-butoxy-1-methyl-ethyl ester, -1-methyl-heptyl ester) (fluroxypyr, -butoxypropyl, -meptyl), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methoxymethyl-pyridine-3-carboxylic acid (imazamox), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), N,N-dimethyl-N-(4-isopropyl-phenyl)-urea (isoproturon), (4-chloro-2-methyl-phenoxy)-acetic acid (MCPA), 2-(4-chloro-2- methyl-phenoxy)-propionic acid (mecoprop), N-(2,6-dichloro-3-methyl-phenyl)-5,7-dimethoxy-1,2,4-triazolo-[1,5-a]-pyrimidine-2-sulphonamide (metosulam), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), 1-amino-N-(1-ethyl-propyl)-3,4-dimethyl-2,6-dinitrobenzene (pendimethalin), methyl 2-[[[(4,5-dihydro-4-methyl-5-oxo-3-propoxy-1H-1,2,4-triazol-1-yl)-carbonyl]-amino]-sulphonyl]-benzoate sodium salt (propoxycarbazone-sodium), ethyl [2-chloro-5-(4-chloro-5-difluoromethoxy-1-methyl-1H-pyrazol-3-yl)-4-fluoro-phenoxy]-acetate (pyraflufen-ethyl), N-(4,6-dimethoxy-pyrimidin-2-yl)-N'-(2-ethylsulphonyl-imidazol 1,2-a]pyridine-3-sulphonamide (sulfosulfuron), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropyl-carbamothioate (triallate), N-methyl-N-(4-methoxy-6-methyl-1,3,5-triazin-2-yl)-N'-(2-methoxycarbonyl-phenylsulphonyl)-urea (tribenuron-methyl), N-[[(4,6-dimethoxy-2-pyrimidinyl)-amino]-carbonyl]-3 2,2,2-trifluoro-ethoxy)-2-pyridinesulphonamide sodium salt (trifloxysulfuron), N-(4-methoxy-6-tri-fluoromethoxy-1,3,5-triazin-2-yl)-N'-(2-trifluoromethyl-phenylsulphonyl)-urea (tritosulfuron).

Surprisingly, it has now been found that the active compound combinations defined above of the 2,6-disubstituted pyridine derivatives of the formula (1) and the active compounds of group 2 listed above, optionally in combination with active compounds of groups 3 and 4, have particularly high herbicidal activity combined with very good compatibility with useful plants and can be used in various crops, in particular in wheat, but additionally also in rice, maize and barley for the selective control of weeds.

Surprisingly, the herbicidal activity of the inventive active compound combinations of compounds of the abovementioned groups 1 and 2 is considerably higher than the sum of the activities of the individual active compounds.

This means that there is not only a complementary action but also an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides.

Furthermore, it has surprisingly been found that the active compound combinations defined above of 2,6-disubstituted pyridine derivatives of the formula (1) and a safener/antidote ("active compounds of group 3") in combination with one or more of the abovementioned active compounds of group 2 have particularly high herbicidal activity combined with very good compatibility with useful plants and can be used in various crops, in particular in cereals and maize, especially wheat, but also in soya, potatoes and rice, for the selective control of weeds.

Moreover, it has surprisingly been found that the safener role described above can also be played by the herbicidally active substance 2,4-dichlorophenoxy-acetic acid (2,4-D) and its derivatives.

The compounds diethyl 1-(2,4-dichlorophenyl)-4,5-dihydro-5-methyl-1H-pyrazole-3,5 -dicarboxylate (mefenpyr-diethyl), 1-methylhexyl [(5-chloro-8-quinolinyl)oxy]acetate (cloquintocet-mexyl) and ethyl 1-(2,4-dichlorophenyl)-5-(trichloromethyl)-1H-1,2,4-triazole-3-carboxylate (fenchlorazole-ethyl) are described in the following patent applications: DE-A-39 39 503, EP-A-191 736 and DE-A-35 25 205. 2,4-D is a known herbicide.

Furthermore, it is surprising that, from a large number of known safeners or antidotes capable of antagonizing the damaging effect of a herbicide on the crop plants, it is specifically the active compounds of group 3 listed above which neutralize the damaging effect of compounds of the formula (I), in combination with one or more of the abovementioned active compounds of group 2, on the crop plants virtually completely without adversely affecting the herbicidal activity against the weeds.

The particularly advantageous effect of the particularly preferred combination partners among the active compounds of group 3, in particular with respect to sparing cereal plants, such as, for example, rice, wheat, barley and rye, as crop plants, may be emphasized here.

The active compound combinations according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Phalaris.*

Monocotyledonous crops of the genera: *Oryza, Zea, Triticum, Hordeum, Avena, Secale, Sorghum, Panicum, Saccharum, Ananas, Asparagus, Allium.*

However, the use of the active compound combinations according to the invention is in no way restricted to these genera, but also extends in the same manner to other plants.

According to the invention, it is possible to treat all plants and parts of plants. By plants are understood here all plants and plant populations, such as desired and undesirable wild plants or crop plants (including naturally occurring crop plants). Crop plants can be plants which can be obtained by conventional breeding and optimization methods or by biotechnological and genetic engineering methods or combinations of these methods, including transgenic plants and including plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested crops and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing on and, in the case of propagation material, in particular in the case of seeds, furthermore by one- or multi-layer coating.

The synergistic effect of the active compound combinations according to the invention is particularly strongly pronounced at certain concentration ratios. However, the ratios by weight of the active compounds in the active compound combinations can be varied within relatively wide ranges. In general, from 0.01 to 1000 parts by weight, preferably from 0.05 to 500 parts by weight and particularly preferably from 0.1 to 100 parts by weight of active compound of group 2 are present per part by weight of active compound of the formula (I).

The advantageous effect of the crop plant compatibility of the active compound combinations according to the invention is likewise particularly strongly pronounced at certain concentration ratios. However, the ratios by weight of the active compounds in the active compound combinations can be varied within relatively wide ranges. In, general, from 0.001 to 1000 parts by weight, preferably from 0.01 to 100 parts by weight and particularly preferably from 0.1 to 10 parts by weight of one of the compounds (antidotes/safeners) mentioned above under (c) which improve the crop plant tolerability are present per part by weight of active compound of the formula (1), its salts or its mixtures with active compounds of group 2.

The active compound combinations can be converted into the customary formulations, such as solutions, emulsions, wettable powders, suspensions, powders, dusts, pastes, soluble powders, granules, suspo-emulsion concentrates, natural and synthetic substances impregnated with active compound, and very fine encapsulations in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water it is also possible to use, for example, organic solvents as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymnethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight, preferably between 0.5 and 90%, of active compounds, including the safeners.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied before and after the plants have emerged, that is to say pre-emergence and post-emergence. They can also be incorporated into the soil before sowing.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20–22, 1967):

If X=% damage by herbicide A (active compound of the formula (I) at an application rate of p kg/ha and Y=% damage by herbicide B (active compound of the formula II) at an application rate of q kg/ha and E=the expected damage of the herbicides A and B at application rates of p and q kg/ha, then $E=X+Y-(X*Y/100)$.

If the actual damage exceeds the calculated value, then the activity of the combination is superadditive, i.e. a synergistic effect exists.

USE EXAMPLES

Customary formulations of the active compounds in question were used. Propoxycarbazone-sodium was used as 70 WG, flufenacet as 60 WG and picolinafen as 75 WG formulation. From the active compounds, an aqueous spray liquor containing 0.1% of the additive Renex-36 was prepared.

Example A

Post-Emergence/Greenhouse

Test plants are grown in a greenhouse under controlled conditions (temperature and light conditions). When the plants have reached a height of 5 to 15 cm, they are sprayed with the test solution. The concentration of the spray liquor is chosen such that the particular amounts of active compound desired are applied in 500 l of water/ha.

After the spray treatment, the plant containers are stored in a greenhouse at constant light and temperature conditions.

After about 3 weeks, the degree of damage to the crop plants is rated in % damage in comparison to the development of the untreated control.

The figures denote:
0%=no damage (like untreated control)
100%=total destruction/damage Active compounds, application rates, test plants and results are shown in the tables below, where the abbreviations used in the tables have the following meaning: ai.= active ingredient=active compound

TABLE A-1

|  | Application rate g of ai/ha | *Avenua* observed | *Avenua* calculated* |
|---|---|---|---|
| flufenacet | 60 | 10 | |
|  | 30 | 10 | |
| picolinafen | 30 | 20 | |
|  | 8 | 0 | |
| flufenacet + picolinafen | 60 + 30 | 70 | 28 |
|  | 30 + 30 | 70 | 28 |
|  | 60 + 8 | 70 | 10 |

*values calculated by the method of Colby

TABLE A-2

|  | Application rate g of ai/ha | *Digitaria* observed | *Digitaria* calculated* |
|---|---|---|---|
| flufenacet | 125 | 10 | |
|  | 60 | 0 | |
| picolinafen | 30 | 50 | |
| flufenacet + picolinafen | 125 + 30 | 90 | 55 |
|  | 60 + 30 | 90 | 50 |

*values calculated by the method of Colby

TABLE A-3

|  | Application rate g of ai/ha | *Echinochloa* observed | *Echinochloa* calculated* |
|---|---|---|---|
| flufenacet | 60 | 60 | |
| picolinafen | 8 | 10 | |
| flufenacet + picolinafen | 60 + 8 | 90 | 64 |

*values calculated by the method of Colby

TABLE A-4

|  | Application rate g of ai/ha | *Cassia* observed | *Cassia* calculated* |
|---|---|---|---|
| flufenacet | 125 | 0 | |
| picolinafen | 30 | 40 | |
| flufenacet + picolinafen | 125 + 30 | 100 | 40 |

*values calculated by the method of Colby

TABLE A-5

|  | Application rate g of ai/ha | *Ipomoea* observed | *Ipomoea* calculated* |
|---|---|---|---|
| flufenacet | 125 | 30 | |
|  | 60 | 30 | |
| picolinafen | 30 | 70 | |
|  | 15 | 70 | |
|  | 8 | 70 | |
| flufenacet + picolinafen | 125 + 30 | 100 | 79 |
|  | 125 + 15 | 100 | 79 |
|  | 125 + 8 | 98 | 79 |
|  | 60 + 8 | 98 | 79 |

*values calculated by the method of Colby

TABLE A-6

|  | Application rate g of ai/ha | *Viola* observed | *Viola* calculated* |
|---|---|---|---|
| flufenacet | 60 | 0 | |
| picolinafen | 8 | 90 | |
| flufenacet + picolinafen | 60 + 8 | 100 | 90 |

*values calculated by the method of Colby

TABLE A-7

|  | Application rate g of ai/ha | *Avenua* observed | *Avenua* calculated* |
|---|---|---|---|
| propoxycarbazone-sodium | 60 | 60 | |
|  | 30 | 50 | |
|  | 15 | 50 | |
| picolinafen | 30 | 20 | |
|  | 15 | 10 | |
| propoxycarbazone-sodium + picolinafen | 60 + 30 | 80 | 68 |
|  | 30 + 30 | 80 | 60 |
|  | 15 + 30 | 80 | 60 |
|  | 60 + 15 | 80 | 64 |
|  | 30 + 15 | 30 | 55 |
|  | 15 + 15 | 80 | 55 |

*values calculated by the method of Colby

TABLE A-8

|  | Application rate g of ai/ha | *Avenua* observed | *Avenua* calculated* |
|---|---|---|---|
| propoxycarbazone-sodium | 30 | 20 | |
|  | 15 | 0 | |
| picolinafen | 30 | 20 | |
|  | 15 | 0 | |
| propoxycarbazone-sodium + picolinafen | 30 + 30 | 50 | 36 |
|  | 30 + 15 | 50 | 20 |
|  | 15 + 15 | 30 | 0 |

*values calculated by the method of Colby

TABLE A-9

| | Application rate g of ai/ha | Avenua observed | Avenua calculated* |
|---|---|---|---|
| propoxycarbazone-sodium | 60 | 0 | |
| | 30 | 0 | |
| | 15 | 0 | |
| picolinafen | 30 | 70 | |
| | 15 | 70 | |
| propoxycarbazone-sodium + picolinafen | 60 + 30 | 80 | 70 |
| | 30 + 30 | 80 | 70 |
| | 15 + 30 | 80 | 70 |
| | 60 + 15 | 90 | 70 |
| | 30 + 15 | 80 | 70 |
| | 15 + 15 | 80 | 70 |

Example B
Outdoor Trials
Cereal
Post-Emergence Spring

To examine a possible synergism, the compounds picolinafen and propoxycarbazone-sodium were tested under outdoor conditions in cereal against economically important weed grasses. The small-plot experiments were conducted on areas used for agricultural cultivation. The selected areas had a high weed content.

The active compounds were applied in spring by the post-emergence method and over the entire area, using spray application with a medium droplet size. To prepare an advantageous preparation of active compound, the active compounds were formulated as 70 WG (70% w/w water-dispersible powder) or 75 WG (75% w/w water-dispersible powder) and suspended in water. The spray liquor was then applied in a water application rate customarily used in practice.

About 8–10 weeks after the application of the spray liquor, the herbicidal activity was scored visually. The figures denote:
0%=no herbicidal effect,
100%=total destruction of the crop or the weeds.

In this experiment, the active compound mixtures showed a highly pronounced synergism in the activity against various weeds. The activity exceeded the value, which was expected for the mixture according to Colby's formula (COLBY 1967), considerably (see the tables below).

TABLE B-1

| | Application rate g of ai/ha | Matricaria ch. observed | | Matricaria ch. calculated* | |
|---|---|---|---|---|---|
| | | 1st location | 2nd location | 1st location | 2nd location |
| propoxycarbazone-sodium | 42 | 60 | 10 | | |
| picolinafen | 75 | 0 | 0 | | |
| propoxycarbazone-sodium + picolinafen | 42 + 75 | 92 | 70 | 60 | 10 |

TABLE B-2

| | Application rate g of ai/ha | Lactuca observed | Lactuca calculated* |
|---|---|---|---|
| propoxycarbazone-sodium | 42 | 10 | |
| picolinafen | 75 | 0 | |
| propoxycarbazone-sodium + picolinafen | 42 + 75 | 70 | 10 |

TABLE B-3

| | Application rate g of ai/ha | Stellaria observed | Stellaria calculated* |
|---|---|---|---|
| propoxycarbazone-sodium | 42 | 30 | |
| picolinafen | 75 | 20 | |
| propoxycarbazone-sodium + picolinafen | 42 + 75 | 62 | 44 |

TABLE B-4

| | Application rate g of ai/ha | Matricaria in. observed | Matricaria in. calculated* |
|---|---|---|---|
| propoxycarbazone-sodium | 42 | 75 | |
| picolinafen | 75 | 45 | |
| propoxycarbazone-sodium + picolinafen | 42 + 75 | 98 | 86 |

TABLE B-5

| | Application rate g of ai/ha | Legousia observed | Legousia calculated* |
|---|---|---|---|
| propoxycarbazone-sodium | 42 | 0 | |
| picolinafen | 75 | 0 | |
| propoxycarbazone-sodium + picolinafen | 42 + 75 | 50 | 0 |

TABLE B-6

| | Application rate g of ai/ha | Galium observed | Galium calculated* |
|---|---|---|---|
| propoxycarbazone-sodium | 42 | 0 | |
| picolinafen | 75 | 30 | |
| propoxycarbazone-sodium + picolinafen | 42 + 75 | 65 | 30 |

TABLE B-2

| | Application rate g of ai/ha | Lactuca observed | Lactuca calculated* |
|---|---|---|---|
| propoxycarbazone-sodium | 42 | 10 | |
| picolinafen | 75 | 0 | |
| propoxycarbazone-sodium + picolinafen | 42 + 75 | 70 | 10 |

What is claimed is:

1. A herbicidal composition comprising an effective amount of an active compound combination comprising (a) N-(4-fluorophenyl)-6-[3-(trifluoromethyl)phenoxy]-2-pyridincarboxamide (picolinafen), and (b) 2-(2-methoxycarbonylphenylsulphonylaminocarbonyl)-4-methyl-5-n-propoxy-2,4-dihydro-3H-1,2,4-triazol-3-one or the sodium salt thereof (propoxycarbazone-sodium).

2. The herbicidal composition of claim 1 additionally comprising at least one crop-plant-compatibility-improving compound selected from the group consisting of 1-methylhexyl 5-chloro-quinoxalin-8-oxy-acetate (cloquintocet), ethyl 1-(2,4-dichloro-phenyl)-5-trichloromethyl-1H-1,2,4-triazole-3-carboxylate (fenchlorazol-ethyl), ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl), 2,4-dichlorophenoxyacetic acid (2,4-D) and derivatives thereof.

3. The herbicidal composition of claim 1 comprising (a) picolinafen, and (b) propoxycarbazone-sodium.

4. The herbicidal composition of claim 1 additionally comprising (c) at least one crop-plant-compatibility-improving compound selected from the group consisting of α-(1,3-dioxolan-2-yl-methoximino)-phenylacetonitrile (oxabetrinil), α-(cyanomethoximino)-phenylacetonitrile (cyometrinil), 4-chloro-N-(1,3-dioxolan-2-yl-methoxy)-α-trifluoro-acetophenoneoxime (fluxofenim), 4,6-dichloro-2-phenyl-pyrimidine (fenclorim), 4-dichloroacetyl-3,4-dihydro-3-methyl-2H-1,4-benzoxazine (benoxacor), 1-methyl-hexyl 5-chloro-quinoxalin-8-oxy-acetate (cloquintocet), 2,2-dichloro-N-(2-oxo-2-(2-propenylamino)-ethyl)-N-(2-propenyl)-acetamide (DKA-24), 1,8-naphthalic anhydride, ethyl 1-(2,4-dichloro-phenyl)-5-trichloromethyl-1H-1,2,4-triazole-3-carboxylate (fenchlorazol-ethyl), phenylmethyl 2-chloro-4-trifluoromethyl-thiazole-5-carboxylate (flurazole), 3-dichloroacetyl-5-(2-furanyl)-2,2-dimethyl-oxazolidine (furilazole, MON-13900), 4-dichloroacetyl-1-oxa-4-aza-spiro[4.5]-decane (AD-67), 2-dichloromethyl-2-methyl-1,3-dioxolane (MG-191), 2,2-dichloro-N-(1,3-dioxolan-2-yl-methyl)-N-(2-propenyl)-acetamide (PPG-1292), 2,2-dichloro-N,N-di-2-propenyl-acetamide (dichlormid), N-(4-methyl-phenyl)-N'-(1-methyl-1-phenyl-ethyl)-urea (dymron), 1-dichloroacetyl-hexahydro-3,3,8a-trimethylpyrrolo[1,2-a]-pyrimidin-6(2H)-one (BAS-145138), N-(2-methoxy-benzoyl)-4-(methylaminocarbonylamino)-benzenesulphonamide, ethyl 4,5-dihydro-5,5-diphenyl-3-isoxazolecarboxylate (isoxadifen-ethyl), diethyl 1-(2,4-dichlorophenyl)-4,5-dihydro-5-methyl-1H-pyrazole-3,5-dicarboxylate (mefenpyr-diethyl) (4-chloro-2-methyl-phenoxy)-acetic acid (MCPA), (+−)-2-(4-chloro-2-methylphenoxy)propanoic acid (mecoprop), 3-dichloroacetyl-2,2,5-trimethyl-oxazolidine (R-29148), 2,4-dichlorophenoxyacetic acid (2,4-D) and derivatives thereof, and optionally (d) one or more compounds selected from the group consisting of 2-chloro-N-(ethoxymethyl)-N-(2-ethyl-6-methyl-phenyl)-acetamide (acetochlor), 5-(2-chloro-4-trifluoromethyl-phenoxy)-2-nitro-benzoic acid sodium salt (acifluorfen-sodium), 2-chloro-6-nitro-3-phenoxy-benzenamine (aclonifen), 2-chloro-N-(methoxymethyl)-N-(2,6-diethyl-phenyl)-acetamide (alachlor), N-ethyl-N'-i-propyl-6-methylthio-1,3,5-triazine-2,4-diamine (ametryn), 4-amino-N-(1,1-dimethyl-ethyl)-4,5-dihydro-3-(1-methyl-ethyl)-5-oxo-1H-1,2,4-triazole-1-carboxamide (amicarbazone), N-(4,6-dimethoxy-pyrimidin-2-yl)-N'-(N-methyl-N-methylsulphonyl-sulphamoyl)-urea (amidosulfuron), 1H-1,2,4-triazol-3-amine (amitrole), 6-chloro-4-ethylamino-2-isopropylamino-1,3,5-triazine (atrazine), 2-[2,4-dichloro-5(2-propynyloxy)-phenyl]-5,6,7,8-tetrahydro-1,2,4-triazolo-[4,3-a]-pyridin-3(2H)-one (azafenidin), N-(4,6-dimethoxy-pyrimidin-2-yl)-N'-[1-methyl-4-(2-methyl-2H-tetrazol-5-yl)-1H-pyrazol-5-ylsulphonyl]-urea (azimsulfuron), N-benzyl-2-(4-fluoro-3-trifluoromethyl-phenoxy)-butanamide (beflubutamide), 4-chloro-2-oxo-3(2H)-benzothiazoleacetic acid (benazolin), N-butyl-N-ethyl-2,6-dinitro-4-trifluoromethyl-benzenamine (benfluralin), N-(4,6-dimethoxy-pyrimidin-2-yl)-N'-(2-methoxycarbonyl-phenylmethylsulphonyl)-urea (bensulfuron), methyl 2-[2-[4-(3,6-dihydro-3-methyl-2,6-dioxo-4-trifluoro-methyl-1(2H)-pyrimidinyl) phenoxy]methyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), ethyl N-benzoyl-N-(3,4-dichloro-phenyl)-DL-alaninate (benzoylprop-ethyl), 3-i-propyl-1H-2,1,3-benzothiadiazin-4(3H)-one (bentazone), methyl 5-(2,4-dichloro-phenoxy)-2-nitro-benzoate (bifenox), 2,6-bis-(4,6-dimethoxy-pyrimidin-2-yloxy)-benzoic acid sodium salt (bispyribac-sodium), 2-bromo-3,3-dimethyl-N-(1-methyl-1-phenyl-ethyl)-butanamide (bromobutide), O-(2,4-dinitro-phenyl) 3,5-dibromo-4-hydroxy-benzaldehyde-oxime (bromofenoxim), 3,5-dibromo-4-hydroxy-benzo-nitrile (bromoxynil), N-butoxymethyl-2-chloro-N-(2,6-diethyl-phenyl)-acetamide (butachlor), [1,1-dimethyl-2-oxo-2-(2-propenyloxy)]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), S-ethyl bis-(2-methyl-propyl)-thiocarbamate (butylate), N,N-diethyl-3-(2,4,6-trimethyl-phenyl-sulphonyl)-1H-1,2,4-triazole-1-carboxamide (cafenstrole), 2-[1-[(3-chloro-2-propenyl)-oxy-imino]-propyl]-3-hydroxy-5-(tetrahydro-2H-pyran-4-yl)-2-cyclohexen-1-one (caloxydim, tepraloxydim), 2-(4-chloro-2-fluoro-5-(2-chloro-2-ethoxycarbonyl-ethyl)-phenyl)-4-difluoromethyl-5-methyl-2,4-dihydro-3H-1,2,4-triazol-3-one (carfentrazone-ethyl), 2,4-dichloro-1-(3-methoxy-4-nitro-phenoxy)-benzene (chlomethoxyfen), 3-amino-2,5-dichloro-benzoic acid (chloramben), N-(4-chloro-6-methoxy-pyrimidin-2-yl)-N'-(2-ethoxycarbonyl-phenylsulphonyl)-urea (chlorimuron-ethyl), 1,3,5-trichloro-2-(4-nitro-phenoxy)-benzene (chlornitrofen), N-(4-methoxy-6-methyl-1,3,5-triazin-2-yl)-N'-(2-chloro-phenylsulphonyl)-urea (chlorsulfuron), N'-(3-chloro-4-methyl-phenyl)-N,N-dimethyl-urea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), N-(4,6-dimethoxy-1,3,5-triazin-2-yl)-N'-(2-(2-methoxy-ethoxy)-phenylsulphonyl)-urea (cinosulfuron), 2-[1-[2-(4-chloro-phenoxy)-propoxyamino]-butyl]-5-(tetrahydro-2H-thiopyran-3-yl)-1,3-cyclohexanedione (clefoxydim), (E,E)-(+)-2-[1-[[(3-chloro-2-propenyl)-oxy]-imino]-propyl]-3-hydroxy-2-cyclohexen-1-one (clethodim), prop-2-ynyl (R)-2-[4-(5-chloro-3-fluoro-pyridin-2-yl-oxy)-phenoxy]-propanoate (clodinafop-propargyl), 3,6-dichloro-pyridine-2-carboxylic acid (clopyralid), methyl 3-chloro-2-[(5-ethoxy-7-fluoro[1,2,4]-triazolo[1,5-c]pyrimidin-2-yl-sulphonyl)-amino]-benzoate (cloransulam-methyl), 2-chloro-4-ethylamino-6-(1-cyano-1-methyl-ethylamino)-1,3,5-triazine (cyanazine), N-(4,6-dimethoxy-pyrimidin-2-yl)-N'-(2-cyclopropylcarbonyl-phenylsulphonyl)-urea (cyclosulfamuron), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), 2,4-dichloro-phenoxyacetic acid (2,4-D), 3,6-dichloro-2-methoxy-benzoic acid (dicamba), (R)-2-(2,4-dichloro-phenoxy)-propanoic acid (dichlorprop-P), methyl-2-[4-(2,4-dichloro-phenoxy)-phenoxy]-propanoate (diclofop-methyl), N-(2,6-dichloro-phenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methyl sulphate (difenzoquat), N-(2,4-difluoro-phenyl)-2-(3-trifluoromethyl-phenoxy)-pyridine-3-carboxamide (diflufenican), 2-[1-[(3,5-difluoro-phenyl)-amino-carbonyl-hydrazono]-ethyl]-pyridine-3-carboxylic acid (diflufenzopyr), S-(1-methyl-1-phenyl-ethyl) 1-piperidine-carbothioate (dimepiperate), (S-)2-chloro-N-(2,4-dimethyl-3-thienyl)-N-(2-methoxy-1-methyl-ethyl)-acetamide (S-) (dimethenamid), 2-amino-4-(1-fluoro-1-methyl-ethyl)-6-(1-methyl-2-(3,5-dimethyl-phenoxy)-ethylamino)-1,3,5-triazine (dimexyflam), N3,N3-diethyl-2,4-dinitro-6-trifluoromethyl-1,3-diamino-benzene (dinitramine), 6,7-dihydro-dipyrido[1,2-a:2',1'-c]pyrazinediium (diquat), S,S-dimethyl 2-difluoromethyl-4-i-butyl-6-trifluoromethyl-pyridine-3,5-dicarbothioate (dithiopyr), N'-(3,4-dichloro-phenyl)-N,N-dimethyl-urea (diuron), 2-[2-(3-chloro-phenyl)-oxiranyl-methyl]-2-ethyl-1H-indene-1,3(2H)-dione (epropodan), S-ethyl dipropylthiocarbamate (EPTC), S-(phenylmethyl) N-ethyl-N-(1,2-dimethyl-propyl)-thiocarbamate (esprocarb), N-ethyl-N-(2-methyl-2-propenyl)-2,6-dinitro-4-trifluoro-methyl-benzenamine (ethalfluralin), 2-ethoxy-1-methyl-2-oxoethyl (S)-(2-ethoxy-1-methyl-2-oxoethyl)-2-chloro-5-(2-chloro-4-trifluoromethyl-phenoxy)-benzoate (ethoxyfen), N-(4,6-dimethoxy-pyrimidin-2-yl)-N'-(2-ethoxy-phenoxy-sulphonyl)-urea (ethoxysulfuron), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamide), isopropyl N-benzoyl-N-(3-chloro-4-fluoro-phenyl)-DL-alaninate (flamprop-isopropyl), isopropyl N-benzoyl-N-(3-chloro-4-fluoro-phenyl)-L-alaninate (flamprop-isopropyl-L), methyl N-benzoyl-N-(3-chloro-4-fluoro-phenoxy)-DL-alaninate (flamprop-methyl), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluoro-benzoate (fluazolate), 4,5-dihydro-3-methoxy-4-methyl-5-oxo-N-[(2-trifluoromethoxy-phenyl)-sulphonyl]-1-H-1,2,4-triazole-1-carboxamide sodium salt (flucarbazone-sodium), N-(2,6-difluoro-phenyl)-5-methyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H-isoindol-2-yl)-phenoxy]-acetate (flumiclorac-pentyl), 2-[7-fluoro-3,4-dihydro-3-oxo-4-(2-propynyl)-2H-1,4-benzoxazin-6-yl]-4,5,6,7-tetrahydro-1H-isoindole-1,3-dione (flumioxazin), 2-[4-chloro-2-fluoro-5-[(1-methyl-2-propynyl)-oxy]-phenyl]4,5,6,7-tetrahydro-1H-isoindole-1,3(2H)-dione (flumipropyn), 3-chloro-4-chloromethyl-1-(3-trifluoromethyl-phenyl)-2-pyrrolidinone (fluorochloridone), ethoxycarbonylmethyl 5-(2-chloro-4-trifluoromethyl-phenoxy)-2-nitro-benzoate (fluoroglycofen-ethyl), 1-(4-chloro-3-(2,2,3,3,3-pentafluoro-propoxymethyl)-phenyl)-5-phenyl-1H-1,2,4-triazole-3-carboxamide (flupoxam), 1-isopropyl-2-chloro-5-(3,6-dihydro-3-methyl-2,6-dioxo-4-trifluoromethyl-1 (2H)-pyrimidyl)-benzoate (flupropacil), N-(4,6-dimethoxy-pyrimidin-2-yl)-N'-(3-methoxycarbonyl-6-trifluoromethyl-pyridin-2-yl-sulphonyl)-urea sodium salt (flupyrsulfuron-methyl-sodium), 9-hydroxy-9H-fluorene-9-carboxylic acid (flurenol), (4-amino-3,5-dichloro-6-fluoro-pyridin-2-yl-oxy)-acetic acid (2-butoxy-1-methyl-ethyl ester, 1-methyl-heptyl ester) (fluroxypyr, -butoxy-propyl, -meptyl), 5-methylamino-2-phenyl-4-(3-trifluoromethyl-phenyl)-3(2H)-furanone (flurtamone), methyl[(2-chloro-4-fluoro-5-(tetrahydro-3-oxo-1H,3H-[1,3,4]-thiadiazolo-[3,4-a]-pyridazin-1-ylidene)-amino)-phenyl]-thio-acetate (fluthiacet-methyl), 5-(2-chloro-4-trifluoromethyl-phenoxy)-N-methylsulphonyl-2-nitro-benzamide (fomesafen), 2-[[[[(4,6-dimethoxy-2-pyrimidinyl)-amino]-carbonyl]-amino]-sulphonyl]-4-formylamino-N,N-dimethyl-benzamide (foramsulfuron), 2-amino-4-(hydroxymethylphosphinyl)-butanoic acid (ammonium salt) (glufosinate-(ammonium)), N-phosphonomethyl-glycine (isopropylammonium salt), (glyphosate, isopropylammonium), (R)-2-[4-(3-chloro-5-trifluoromethyl-pyridin-2-yl-oxy)-phenoxy]-propanoic acid (methyl ester, 2-ethoxy-ethyl ester, butyl ester) (haloxyfop, -methyl, -P-methyl, -ethoxyethyl, -butyl), 3-cyclohexyl-6-dimethylamino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methyl-benzoate (imazamethabenz-methyl), 2-(4,5-dihydro-4-methyl-4-isopropyl-5-oxo-1H-imidazol-2-yl)-5-methyl-pyridine-3-carboxylic acid (imazamethapyr), 2-(4,5-dihydro-4-methyl-4-isopropyl-5-oxo-1H-imidazol-2-yl)-5-methoxymethyl-pyridine-3-carboxylic acid (imazamox), 2-(4,5-dihydro-4-methyl-4-isopropyl-5-oxo-1H-imidazol-2-yl)quinoline-3-carboxylic acid (imazaquin), 2-(4,5-dihydro-4-methyl-4-i-propyl-5-oxo-1H-imidazol-2-yl)-5-ethyl-pyridine-3-carboxylic acid (imazethapyr), N-(4,6-dimethoxy-pyrimidin-2-yl)-N'-(2-chloro-imidazo[1,2-a]-pyridin-3-yl-sulphonyl)-urea (imazosulfuron), N-(4-methoxy-6-methyl-1,3,5-triazin-2-yl)-N'-(5-iodo-2-methoxycarbonyl-phenyl-sulphonyl)-urea sodium salt (iodosulfuron-methyl-sodium), 4-hydroxy-3,5-diiodo-benzonitrile (ioxynil), N,N-dimethyl-N'-(4-isopropyl-phenyl)-urea (isoproturon), N-(3-(1-ethyl-1-methyl-propyl)-isoxazol-5-yl)-2,6-dimethoxy-benzamide (isoxaben), (4-chloro-2-methylsulphonyl-phenyl)-(5-cyclopropyl-isoxazol-4-yl)-methanone (isoxachlortole), (5-cyclopropyl-isoxazol-4-yl)-(2-methylsulphonyl-4-trifluoromethyl-phenyl)-methanone (isoxaflutole), 2-[2-[4 -[(3,5-dichloro-2-pyridinyl)-oxy]-phenoxy]-1-oxo-propyl]-isoxazolidine (isoxapyrifop), (2-ethoxy-1-methyl-2-oxo-ethyl)-5-(2-chloro-4-trifluoromethyl-phenoxy)-2-nitro-benzoate (lactofen), N'-(3,4-dichloro-phenyl)-N-methoxy-N-methyl-urea (linuron), (4-chloro-2-methyl-phenoxy)-acetic acid (MCPA), 2-(4-chloro-2-methyl-phenoxy)-propionic acid (mecoprop), 2-(2-benzothiazol-yloxy)-N-methyl-N-phenyl-acetamide (mefenacet), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), 2-chloro-N-(2,6-dimethyl-phenyl)-N-(1H-pyrazol-1-yl-methyl)-acetamide (metazachlor), N'-(4-(3,4-dihydro-2-methoxy-2,4,4-trimethyl-2H-1-benzopyran-7-yl-oxy)-phenyl)-N-methoxy-N-methyl-urea (metobenzuron), N'-(4-bromo-phenyl)-N-methoxy-N-methyl urea (metobromuron), (S)-2-chloro-N-(2-ethyl-6-methyl-phenyl)-N-(2-methoxy-1-methyl-ethyl)-acetamide (metolachlor, S-metolachlor), N-(2,6-dichloro-3-methyl-phenyl)-5,7-dimethoxy-1,2,4-triazolo[1,5-a]-pyrimidine-2-sulphonamide (metosulam), N'-(3-chloro-4-methoxy-phenyl)-N,N-dimethyl-urea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonyl-phenylsulphonyl)-urea (metsulfuron-methyl), S-ethyl-hexahydro-1H-azepine-1-carbothioate (molinate), 2-(2-naphthyloxy)-N-phenyl-propanamide (naproanilide), N-butyl-N'-(3,4-dichloro-phenyl)-N-methyl-urea (neburon), N-(4,6-dimethoxy-pyrimidin-2-yl)-N'-(3-dimethylcarbamoyl-pyridin-2-yl-sulphonyl)-urea (nicosulfuron), S-(2-chloro-benzyl)-N,N-diethyl-thiocarbamate (orbencarb), 4-dipropylamino-3,5-dinitro-benzenesulphonamide (oryzalin), 3-[2,4-dichloro-5-(2-propynyl-oxy)-phenyl]-5-(t-butyl)-1,3,4-oxadiazol-2 (3H)-one (oxadiargyl), 3-[2,4-dichloro-5-(1-methyl-ethoxy)-phenyl]-5-(t-butyl)-1,3,4-oxadiazol-2(3H)-one (oxadiazon), N-(4,6-dimethyl-pyrimidin-2-yl)-N'-(2-oxetan-3-yl-oxycarbonyl-phenylsulphonyl)-urea (oxasulfuron), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethylbenzene (oxyfluorfen), 1,1'-dimethyl-4,4'-bipyridinium (paraquat), 1-amino-N-(1-ethyl-propyl)-3,4-dimethyl-2,6-dinitro-benzene (pendimethalin), 4-(t-butyl)-N-(1-ethyl-propyl)-2,6-dinitro-benzenamine (pendralin), 4-amino-3,5,6-trichloro-pyridine-2-carboxylic acid (picloram), 2-chloro-N-(2,6-diethyl-phenyl)-N-(2-propoxy-ethyl)-acetamide (pretilachlor), N-(4,6-bisdifluoromethoxy-pyrimidin-2-yl)-N'-(2-methoxy-carbonyl-phenylsulphonyl)-urea (primisulfuron-methyl), 1-chloro-N-[2-chloro-4-fluoro-5-[(6S,7aR)-6-fluoro-tetrahydro-1,3-dioxo-1H-pyrrolo[1,2-c]imidazol-2-(3H)-yl]-phenyl]-methanesulphonamide (profluazol), 2-chloro-N-isopropyl-N-phenyl-acetamide (propachlor), N-(3,4-dichloro-phenyl)-propaneamide (propanil), (R)-[2-[[(1-methyl-ethylidene)-amino]-oxy]-ethyl]-2-[4-(6-chloro-2-quinoxalinyloxy)-phenoxy]-propanoate (propaquizafop), 2-chloro-N-(2-ethyl-6-methyl-phenyl)-N-[(1-methyl-ethoxy)-methyl]-acetamide (propisochlor), S-phenylmethyl N,N-dipropyl-thiocarbamate (prosulfocarb), N-(4-methoxy-6-methyl-1,3,5-triazin-2-yl)-N'-(2-(3,3,3-trifluoro-propyl)-phenylsulphonyl)-urea (prosulfuron), ethyl[2-chloro-5-(4-chloro-5-difluoromethoxy-1-methyl-1H-pyrazol-3-yl)-4-fluoro-phenoxy]-acetate (pyraflufen-ethyl), 1-(3-chloro-4,5,6,7-tetrahydro-pyrazolo[1,5-a]pyridin-2-yl)-5-(methyl-2-propynylamino)-1H-pyrazole-4-carbonitrile (pyrazogyl), 4-(2,4-dichloro-benzoyl)-1,3-dimethyl-5-(4-methyl-phenylsulphonyloxy)-pyrazole (pyrazolate), 4-(2,4-dichloro-benzoyl)-1,3-dimethyl-5-(phenylcarbonylmethoxy)-pyrazole (pyrazoxyfen), N-(4,6-dimethoxy-pyrimidin-2-yl)-N'-(4-ethoxycarbonyl-1-methyl-pyrazol-5-yl-sulphonyl)-urea (pyrazosulfuron-ethyl), O-[2,6-bis-(4,6-dimethoxy-pyrimidin-2-yl-oxy)-benzoyl] diphenylmethanone-oxime (pyribenzoxim), 6-chloro-3-phenyl-4-pyridazinol (pyridafol), O-(6-chloro-3-phenyl-pyridazin-4-yl) S-octyl thiocarbonate (pyridate), 6-chloro-3-phenylpyridazin-4-ol (pyridatol), 7-[(4,6-dimethoxy-2-pyrimidinyl)-thio]-3-methyl-1 (3H)-isobenzofuranone (pyriftalid), methyl 2-(4,6-dimethoxy-pyrimidin-2-yl-oxy)-benzoate (pyriminobac-methyl), 2-chloro-6-(4,6-dimethoxy-pyrimidin-2-ylthio)-benzoic acid sodium salt (pyrithiobac-sodium), 3,7-dichloro-quinoline-8-carboxylic acid (quinchlorac), 7-chloro-3-methyl-quinoline-8-carboxylic acid (quinmerac), 2-[4-(6-chloro-2-quinoxalinyloxy)-phenoxy]-propanoic acid (ethyl ester, tetrahydro-2-furanyl-methyl ester) (quizalofop, -ethyl, -P-ethyl, -P-tefuryl), N-(4,6-dimethoxy-pyrimidin-2-yl)-N'-(3-ethylsulphonyl-pyridin-2-yl-sulphonyl)-urea (rimsulfuron), 2-(1-ethoximinobutyl)-5-(2-ethylthiopropyl)-3-hydroxy-2-cyclohexen-1-one (sethoxydim), 6-chloro-2,4-bis-ethylamino-1,3,5-triazine (simazin), 2-(2-chloro-4-methylsulphonyl-benzoyl)-cyclohexane-1,3-dione (sulcotrione), 2-(2,4-dichloro-5-methylsulphonylamino-phenyl)-4-difluoromethyl-5-methyl-2,4-dihydro-3H-1,2,4-triazol-3-one (sulfentrazone), N-phosphonomethyl-glycine-trimethylsulphonium (sulfosate), N-(4,6-dimethoxy-pyrimidin-2-yl)-N'-(2-ethyl-sulphonyl)-imidazo[1,2-a]pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethyl-phenyl)-N-(3-methoxy-2-thienyl-methyl)-acetamide (thenylchlor), methyl 2-difluoromethyl-5-(4, 5-dihydro-thiazol-2-yl)-4-(2-methyl-propyl)-6-trifluoro-methyl-pyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propynyl)-2H-1,4-benzoxazin-3(4H)-one (thidiazimin), N-(4-methoxy-6-methyl-1,3,5-triazin-2-yl)-N'-(2-methoxycarbonyl-thien-3-yl-sulphonyl)-urea (thifensulfuron-methyl), 2-(ethoximino-propyl)-3-hydroxy-5-(2,4,6-trimethyl-phenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloro-ethoxy)-phenylsulphonyl]-urea (triasulfuron), N-methyl-N-(4-methoxy-6-methyl-1,3,5-triazin-2-yl)-N'-(2-methoxycarbonyl-phenylsulphonyl)-urea (tribenuron-methyl), (3,5,6-trichloro)-pyridin-2-yl-oxy-acetic acid (triclopyr), 2-(3,5-dichloro-phenyl)-2-(2,2,2-trichloro-ethyl)-oxirane (tridiphane), N-[[(4,6-dimethoxy-2-pyrimidinyl)-amino]-carbonyl]-3-(2,2,2-trifluoro-ethoxy)-2-pyridinesulphonamide sodium salt (trifloxysulfuron), 1-amino-2,6-dinitro-N,N-dipropyl-4-trifluoromethyl-benzene (trifluralin), N-[4-dimethylamino-6-(2,2,2-trifluoro-ethoxy)-1,3,5-triazin-2-yl]-N'-(2-methoxycarbonyl-phenyl-sulphonyl)-urea (triflusulfuron-methyl), N-(4-methoxy-6-trifluoromethyl-1,3,5-triazin-2-yl)-N'-(2-trifluoro-methyl-phenylsulphonyl)-urea (tritosulfuron), 2-pyridinesulphonamide N-[[(4,6-dimethoxy-2-pyrimidinyl)amino]carbonyl]-3-(N-methyl-N-methylsulphonyl-amino), methyl 2-[[[[(4,6-dimethoxy-2-pyrimidinyl)amino]carbonyl]amino] sulphonyl]-4-[[(methylsulphonyl)amino]methyl] benzoate and 4-[4,5-dihydro-4-methyl-5-oxo-(3-trifluoromethyl)-1H-1,2,4-triazol-1-yl]-2-[(ethylsulphonyl)-amino]-5-fluoro-benzenecarbothioamide.

5. The herbicidal composition of claim 1 additionally comprising
(d) one or more compounds selected from the group consisting of 2,6-bis-(4,6-dimethoxy-pyrimidin-2-yl-oxy)-benzoic acid sodium salt (bispyribac-sodium), N-(2,6-difluoro-phenyl)-8-fluoro-5-methoxy-[1,2,4]-triazolo-[1,5-c]-pyrimidine-2-sulphonamide (florasulam), N-(4,6-dimethoxy-pyrimidin-2-yl)-N'-(3-methoxy-carbonyl-trifluoromethyl-pyrid-2-yl-sulphonyl)-urea sodium salt (flupyrsulfron-methyl-sodium), N,N-dimethyl-N'-(4-isopropyl-phenyl)-urea (isoproturon), N-(2,6-dichloro-3-methyl-phenyl)-5,7-dimethoxy-1,2,4-triazolo[1,5-a]pyrimidine-2-sulphonamide (metosulam), 1-amino-N-(1-ethyl-propyl)-3,4-dimethyl-2,6-dinitro-benzene (pendimethalin), and ethyl-[2-chloro-5-(4-chloro-5-difluoromethoxy-1-methyl-1H-pyrazol-3-yl)-4-fluoro-phenoxy]acetate (pyraflufen-ethyl).

\* \* \* \* \*